United States Patent [19]

Plath et al.

Best Available Copy

[11] 4,298,749

[45] Nov. 3, 1981

[54] PYRAZOLE ETHER DERIVATIVES

[75] Inventors: Peter Plath, Ludwigshafen; Wolfgang Rohr, Mannheim; Bruno Wuerzer, Limburgerhof; Rainer Becker, Bad Durkheim, all of Fed. Rep. of Germany

[73] Assignee: BASF Aktiengesellschaft, Fed. Rep. of Germany

[21] Appl. No.: 127,088

[22] Filed: Mar. 4, 1980

Related U.S. Application Data

[62] Division of Ser. No. 49,506, Jun. 18, 1979, abandoned.

[30] Foreign Application Priority Data

Jul. 4, 1978 [DE] Fed. Rep. of Germany ....... 2829289

[51] Int. Cl.$^3$ .................... C07D 231/20; C07D 231/22

[52] U.S. Cl. ........................................ 548/377; 71/92; 71/90; 548/374; 548/262; 548/129; 548/336; 546/211; 548/240

[58] Field of Search ......................................... 548/377

[56] References Cited

U.S. PATENT DOCUMENTS

| | | | |
|---|---|---|---|
| 3,882,142 | 5/1975 | Walworth et al. | 71/92 |
| 3,922,161 | 11/1975 | Walworth et al. | 71/92 |

FOREIGN PATENT DOCUMENTS

| | | |
|---|---|---|
| 1542836 | 4/1971 | Fed. Rep. of Germany . |
| 2260485 | 6/1973 | Fed. Rep. of Germany . |
| 2513750 | 10/1975 | Fed. Rep. of Germany . |

OTHER PUBLICATIONS

Sandstrom I, Chem. Abst. 1956, vol. 50, pp. 12029-12030.
Sandstrom II, Chem. Abst. 1963, vol. 59, p. 3929.
Kobayashi et al., Chem. Abst. 1975, vol. 83, No. 206254h.
Taylor et al., Chem. Abst. 1978, vol. 88, No. 74337d.

*Primary Examiner*—Henry R. Jiles
*Assistant Examiner*—Natalia Harkaway
*Attorney, Agent, or Firm*—Keil & Witherspoon

[57] ABSTRACT

Substituted pyrazole ether derivatives, and salts thereof, having a herbicidal action, herbicides containing these compounds as active ingredients, and processes for controlling the growth of unwanted plants with these compounds.

2 Claims, No Drawings

PYRAZOLE ETHER DERIVATIVES

This is a division of application Ser. No. 49,506, filed June 18, 1979, now abandoned.

The present invention relates to novel and valuable substituted pyrazole ether derivatives, and salts thereof, having a herbicidal action, herbicides containing these compounds as active ingredients, and processes for controlling the growth of unwanted plants with these compounds.

The use of substituted pyrazoles and pyrazolium salts, e.g., 1,2-dimethyl-3,5-diphenylpyrazolium methyl-sulfate, as herbicides has been disclosed (German Laid-Open Applications DE-OS Nos. 2,513,750 and 2,260,485). Further, the prior art agent 3-isopropyl-2,1,3-benzothiadiazin-4-one-2,2-dioxide (German No. 1,542,836) is used in large amounts in practice as a herbicide.

We have now found that pyrazole ether derivatives of the formula

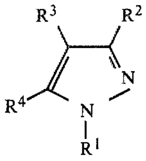

(1), where $R^1$ denotes hydrogen, cyano, an unsubstituted aliphatic hydrocarbon radical, an aliphatic hydrocarbon radical mono- or polysubstituted by halogen, hydroxy, acyloxy, alkoxy, alkylthio, alkoxycarbonyl, alkylaminocarbonal or by dialkylaminocarbonyl, $R^1$ further denotes acetoacetyl, alkylaminosulfonyl, alkylsulfonyl, arylsulfonyl or

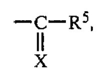

X denoting oxygen or sulfur and $R^5$ denoting hydrogen, alkoxyalkyl, alkyl, haloalkyl, aralkyl or aryl which is unsubstituted or mono- or polysubstitued by halogen, cyano, nitro, alkyl, alkoxy, alkylthio, haloalkyl, alkoxycarbonyl or alkoxycarbonylamino, $R^1$ further denotes

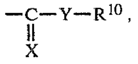

X and Y being identical or different and denoting oxygen or sulfur, and $R^{10}$ having the same meanings as $R^5$, $R^1$ further denotes

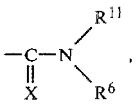

X denoting oxygen or sulfur, $R^{11}$ having the same meanings as $R^5$ and $R^6$ denoting hydrogen or having the same meanings as $R^5$, $R^2$ denotes Y-$R^7$, Y denoting oxygen or sulfur and $R^7$ denoting an aliphatic, cycloaliphatic or araliphatic hydrocarbon radical, a heterocyclic radical or an aryl radical, these radicals being unsubstituted or mono- or polysubstituted by alkyl, halogen, haloalkyl, cycloalkyl, aryloxy, alkoxy, alkylthio, nitro, cyano, alkylaminocarbonyl, dialkylaminocarbonyl, acyloxy, acylamino, O-alkylcarbonyl, S-alkylcarbonyl, aryl or a heterocycle, $R^3$ denotes halogen, cyano, nitro or

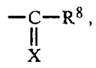, 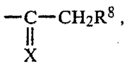, 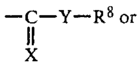 or 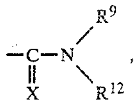,

X and Y being identical or different and denoting oxygen or sulfur, $R^8$ denotes an aliphatic, cycloaliphatic or araliphatic hydrocarbon radical, an aryl radical or a heterocyclic radical, these radicals being unsubstituted or substituted by halogen, cyano, haloalkyl, alkoxy or alkylthio, and $R^9$ and $R^{12}$ being identical or different and denoting hydrogen or methyl, and $R^4$ denotes hydrogen, alkyl, halogen, alkoxy, alkylthio, cyano, haloalkyl, alkoxycarbonyl, unsubstituted phenyl, or alkyl- or halogen-substituted phenyl, and salts of such pyrazole ether derivatives, have a good herbicidal action and are tolerated well by crop plants.

Salts are those with inorganic or organic acids, e.g., hydrochloric acid, orthophosphoric acid, sulfuric acid, formic acid, trichloracetic acid, methanesulfonic acid, p-toluenesulfonic acid and dodecylbenzenesulfonic acid.

The new pyrazole ether derivatives are usually in isomer form:

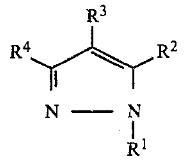 and 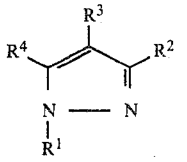

The isomer ratio is determined essentially by the various substituents.

Unless it is specifically mentioned in the following that only one of the two isomers is present, the isomer mixture shall always be meant by a certain formula or designation.

Examples of meanings for $R^1$ in the general formula are hydrogen, cyano, linear or branched alkyl of 1 to 6 carbon atoms which is unsubstituted or mono- or polysubstituted by fluoro, chloro, bromo, hydroxy, acyloxy (with 2 to 4 carbon atoms in the acyl), alkoxy or alkylthio (with 1 to 4 carbon atoms in the alkyl), or by alkoxycarbonyl, alkylaminocarbonyl or dialkylaminocarbonyl (each with 1 to 3 carbon atoms in the alkyl).

$R^1$ may also for instance denote acyl, such as acetoacetyl, methanesulfonyl, p-toluenesulfonyl, methylaminosulfonyl, or the acyl radicals

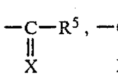, 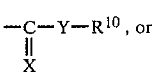, or 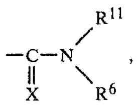,

X and Y being identical or different and denoting oxygen or sulfur and $R^5$, $R^{10}$ and $R^{11}$ denoting for instance linear or branched alkyl of 1 to 16 carbon atoms which is unsubstituted or substituted by halogen, cyano, alkoxy or alkylthio of 1 to 4 carbon atoms.

$R^5$, $R^{10}$ and $R^{11}$ may also denote for instance linear or branched alkenyl of 2 to 6 carbon atoms which is unsubstituted or chloro-substituted, cycloalkyl of 3 to 8 carbon atoms, or aralkyl (with 1 to 3 carbon atoms in the alkyl and 6 to 10 carbon atoms in the aryl) which is unsubstituted or mono- or polysubstituted by fluoro, chloro, bromo, alkyl, alkoxy or haloalkyl of 1 to 4 carbon atoms.

Finally, $R^5$, $R^{10}$ and $R^{11}$ may also denote for example aryl of 6 to 10 carbon atoms which is unsubstituted or mono- or polysubstituted by fluoro, chloro, bromo, alkyl, alkoxy, alkylthio and haloalkyl of 1 to 4 carbon atoms, alkoxycarbonyl and alkoxycarbonylamino (=-NH-$CO_2$-Alk) of 1 to 3 carbon atoms in the alkyl, or by nitro or cyano.

$R^6$ denotes for instance hydrogen or linear or branched alkyl of 1 to 3 carbon atoms.

$R^2$ denotes the group -Y-$R^7$, Y denoting oxygen or sulfur and $R^7$ denoting for example linear or branched alkyl of 1 to 18 carbon atoms which is unsubstituted or mono- or polysubstituted by fluoro, chloro, bromo, cyano, nitro, cycloalkyl, alkoxy or alkylthio of 1 to 4 carbon atoms; unsubstituted or fluoro-, chloro-, methoxy-, methyl- or trifluoromethyl-substituted aryloxy of 6 to 10 carbon atoms in the aryl; alkoxycarbonyl, alkylaminocarbonyl or dialkylaminocarbonyl of 1 to 4 carbon atoms in the alkyl; acyloxy of 2 to 4 carbon atoms in the acyl; or by saturated or unsaturated five- or six-membered heterocyclic compounds containing up to 3 hetero atoms which may be identical or different.

Preferred five-membered heterocycles are pyrazole, imidazole, furan, thiophene, tetrahydrofuran, isoxazole, 1,3-dioxolane, 1,2,4-triazole and 1,3,4-thiadiazole; preferred six-membered heterocycles are piperidine, pyridine and tetrahydropyran.

$R^7$ may also denote linear or branched alkenyl of 3 to 18 carbon atoms which is unsubstituted or mono- or polysubstituted by chloro, or cycloalkyl of 3 to 8 carbon atoms which is unsubstituted or mono- or polysubstituted by alkyl, alkoxy, haloalkyl of 1 to 4 carbon atoms, fluoro, chloro or bromo.

$R^7$ may further denote for instance aralkyl of 1 to 3 carbon atoms, in the alkyl and 6 to 10 carbon atoms in the aryl and which is unsubstituted or mono- or polysubstituted by alkyl, alkylthio, alkoxy, haloalkyl, alkoxycarbonyl of 1 to 4 carbon atoms, fluoro, chloro or bromo; aryl of 6 to 10 carbom atoms which is unsubstituted or mono- or polysubstituted by fluoro, chloro, bromo, cyano, trifluoromethyl, nitro, or by alkyl, alkoxy, alkylthio, alkoxycarbonyl, alkylaminocarbonyl or dialkylaminocarbonyl, each alkyl being of 1 to 4 carbon atoms; aryl of 6 to 10 carbon atoms which is substituted by phenyl or phenoxy which in turn may be substituted by fluoro or chloro; or phenyl substituted by lower ($C_1$ to $C_4$) alkyl esters of (thio)-glycolic acid or (thio)-lactic acid via a (thio)-ether bond.

Further, $R^7$ may for example denote heterocyclic 5- or 6-membered rings, such as 3-tetrahydrofurfuryl, 4-piperidyl and 2-(1,3,4)-thiadiazole.

$R^3$ for instance denotes halogen, especially chlorine and bromine, cyano, nitro or, preferably,

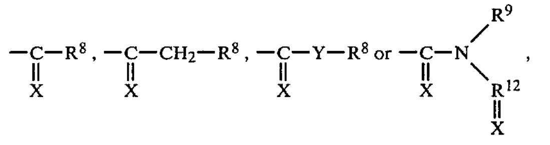

X and Y being oxygen or sulfur, $R^9$ and $R^{12}$ being hydrogen or methyl, $R^8$ being linear or branched alkyl of 1 to 6 carbon atoms which is unsubstituted or mono- or polysubstituted by fluoro, chloro, cyano, methoxy or trifluoromethyl, or being for instance cycloalkyl of 3 to 6 carbon atoms, or phenyl or benzyl which is unsubstituted or mono- or polysubstituted by fluoro, chloro, bromo, trifluoromethyl, cyano, methoxy or methylthio.

When $R^3$ denotes for example

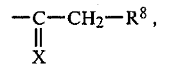

$R^8$ may also be a 5- or 6-membered heterocyclic ring which may be saturated or aromatic, e.g. tetrahydrofuran, pyrazole, imidazole, 1,2,4-triazole, and piperidine.

$R^4$ denotes for example hydrogen, linear or branched alkyl of 1 to 6 carbon atoms, cycloalkyl of 3 to 6 carbon atoms, chloro, bromo, cyano, alkoxy of alkylthio of 1 to 3 carbon atoms, trifluoromethyl, alkoxycarbonyl of 1 to 3 carbon atoms, and phenyl which is unsubstituted or mono- or polysubstituted by methyl fluoro and chloro.

The preparation of the new pyrazole ether derivatives is described in more detail below.

The compounds can be manufactured by processes known from the literature, e.g., Ark. Kemi, 4, 297–323, 1952, Ark. Kemi, 8, 523–544, 1955, and Chem. Ber., 92, 2593, 1959.

When $R^1$ is hydrogen, $R^2$ is methoxy, $R^3$ is ethoxycabonyl and $R^4$ is methyl, the reaction may be represented by the formula scheme (2):

(2)

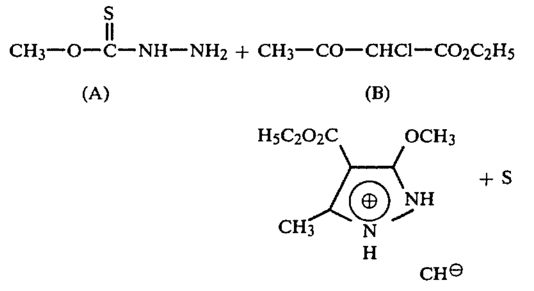

The pyrazole ether derivative obtained as hydrochloride is neutralized by conventional methods and separated from elemental sulfur by extraction or recrystallization. The thiocarbonic acid alkyl ester hydrazide (A) required as intermediate may be prepared by conventional methods, e.g., Acta chem. Scand., 23, 1916–1934, 1969.

The manufacture of 2-chloro-1,3-dicarbonyl compounds such as (B) is also known, e.g., by reaction of the β-dicarbonyl compound with sulfuryl chloride.

The following examples illustrate the method of manufacture.

EXAMPLE 1

3-(3,3,5-trimethylcyclohexyloxy)-5-methyl-4-methoxycarbonyl-pyrazole

At 100° C., 128 g of 3,3,5-trimethylcyclohexanol is introduced into a suspension of 18 g of sodium hydride (80 wt% in paraffin oil). The mixture is boiled until no more hydrogen evolves. After the mixture has cooled, 46 g of carbon disulfide is dripped in, and the whole is stirred for 1 hour at room temperature (20° C.). 250 ml of water is then added, the resultant mixture is vigorously stirred, and the aqueous solution is separated. The aqueous xanthate solution obtained is placed in a stirred flask and 70 g of sodium chloroacetate is added. After the mixture has been stirred for 12 hours at room temperature, 60 g of hydrazine hydrate is run in while stirring, and stirring is continued for a further 4 hours at room temperature. The oil which separates out is extracted with methylene chloride and dried over sodium sulfate.

The solvent is evaporated, leaving an oil (120 g, $n_D^{25}=1.5100$) whose composition ($C_{10}H_{20}N_2OS$) is proved by combustion analysis and nmr spectroscopy.

At room temperature and while stirring, 84 1 g of methyl 2-chloroacetate is added to a solution, in 250 ml of acetonitrile, of the thiocarbazic acid-O-(3,3,5-trimethylcyclohexyl)-ester obtained in this manner. After stirring for 12 hours at room temperature, the mixture of solids which has precipitated out is separated by filtration and washed with acetone. The solids mixture is then stirred into 200 ml of aqueous ammonia solution (12 wt%) and subsequently extracted twice with methylene chloride (150 ml each time). After the methylene chloride solution has been dried over sodium sulfate, the solvent is evaporated. The solid which remains has, after recrystallization from a 2:1 mixture of toluene and n-hexane, a melting point of 167° to 168° C. and has, according to combustion analysis and nmr spectroscopy, the composition:

$C_{15}H_{24}N_2O_3$ 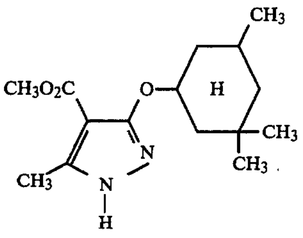

EXAMPLE 2

3-Benzylthio-5-methyl-4-methoxycarbonyl pyrazole

At room temperature, 47 g of methyl 2-chloroacetate is added to a solution of 55 g of dithiocarbazic acid-S-benzyl ester in 250 ml of tetrahydrofuran. After stirring for 16 hours at room temperature, the precipitated solids mixture is filtered and washed with diethyl ether, and the residue is stirred into 200 ml of 12% strength ammonia solution. The product has the sulfur removed from it by extraction with methylene chloride. After drying over sodium sulfate, the methylene chloride is distilled off and the solid which remains is recrystallized from ethyl acetate. Melting point: 109°-110° C.

EXAMPLE 3

Acetate of 3-(2',3'-dimethylphenoxy)-5-methyl-4-methoxycarbonyl pyrazole 15 g of 3-(2',3'-dimethylphenoxy)-5-methyl-4-methoxycarbonyl pyrazole is added to 25 g of acetic anhydride and the mixture is boiled for 5 minutes. After cooling, 150 ml of water is added and the mixture vigorously stirred for 30 minutes. After filtration and drying, a white solid (m.p. 111° C.) is obtained in almost quantitative yield.

EXAMPLE 4

1,4-Bis-(methoxycarbonyl)-3-(2',3'-dimethylphenoxy)-5-methyl pyrazole

A mixture of 5.6 g of triethylamine, 13 g of 3-(2',3'-dimethylphenoxy)-5-methyl-4-methoxycarbonyl pyrazole and 100 ml of tetahydrofuran is prepared, and, while stirring and cooling, 4.9 g of methyl chlorocarbonate is dripped in. After stirring for 16 hours, the precipitated hydrochloride is filtered off. The filtrate is concentrated and the residue is recrystallized from ethyl acetate. Melting point: 115° C.

The following compounds were obtained analogously:

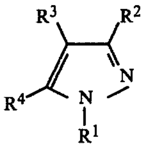

| No. | $R^1$ | $R^2$ | $R^3$ | $R^4$ | m.p. (°C.) |
|---|---|---|---|---|---|
| 5 | hydrogen | $-O-CH_3$ | $-CO_2CH_3$ | $CH_3$ | |
| 6 | " | $-O-C_2H_5$ | " | " | |
| 7 | " | $-O-C_3H_7-i$ | " | " | 125-126 |
| 8 | " | $-O-C_4H_9-n$ | " | " | |
| 9 | " | $-O-C_4H_9-$sec. | " | " | 65-67 |
| 10 | " | $-O-C_4H_9-$iso | " | " | 86 |
| 11 | " | $-O-C_4H_9-$tert. | " | " | |
| 12 | acetyl | $-O-C_4H_9-$sec. | " | " | 83 |
| 13 | chloroacetyl | $-O-C_4H_9-$sec. | " | " | |
| 14 | dichloroacetyl | " | " | " | |
| 15 | acetyl | $-O-C_3H_7-i$ | " | " | 58-59 |
| 16 | propionyl | " | " | " | |
| 17 | methoxyacetyl | " | " | " | |
| 18 | hydroxymethyl | " | " | " | |
| 19 | acetoxyacetyl | $-O-C_4H_9-$iso | " | " | |
| 20 | acetoacetyl | " | " | " | |
| 21 | methoxycarbonyl | " | " | " | |
| 22 | isopropoxycarbonyl | " | " | " | |
| 23 | phenoxycarbonyl | " | " | " | 104-105 |
| 24 | $-CH_2-CONHCH_3$ | " | " | " | |
| 25 | $-CH_2-CO_2CH_3$ | " | " | " | |
| 26 | $-SO_2-CH_3$ | " | " | " | |

-continued

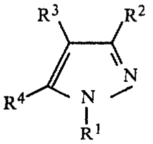

| No. | $R^1$ | $R^2$ | $R^3$ | $R^4$ | m.p. (°C.) |
|---|---|---|---|---|---|
| 27 | 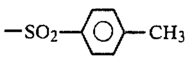 | " | " | " | |
| 28 | $SO_2$—NH—$CH_3$ | " | " | " | |
| 29 | —CO—S—$C_3H_7$—i | " | " | " | |
| 30 | —CS—N$(CH_3)_2$ | 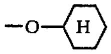 | " | " | |
| 31 | 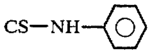 | " | " | " | |
| 32 | —CO—$NHCH_3$ | " | " | " | |
| 33 | 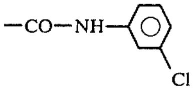 | " | " | " | |
| 34 | 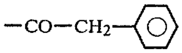 | " | " | " | |
| 35 | 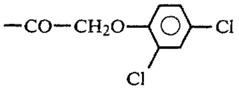 | " | " | " | |
| 36 | —CN | " | " | " | |
| 37 | 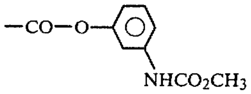 | " | " | " | |
| 38 | benzoyl | " | " | " | |
| 39 | 2',4'-dichlorobenzoyl | " | " | " | |
| 40 | hydrogen | " | " | " | 123 |
| 41 | acetyl | " | " | " | |
| 42 | phenoxycarbonyl | " | " | " | 104-106 |
| 43 | 3'-chlorophenoxy-carbonyl | " | " | " | |
| 44 | hydrogen | —S—$C_3H_7$—i | " | " | 117-119 |
| 45 | phenoxycarbonyl | " | " | " | |
| 46 | 3'-chlorophenoxy-carbonyl | " | " | " | |
| 47 | hydrogen | —O—$C_3H_7$—i | —$CO_2C_3H_7$—i | " | amorphous |
| 48 | hydrogen | 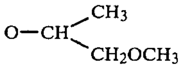 | —$CO_2CH_3$ | " | oil, $n_D^{30}$ = 1.4800 |
| 49 | hydrogen | cyclopentyl-methyloxy | " | " | 84 |
| 50 | " | 2-pentyloxy | " | " | oil, $n_D^{23}$ = 1.4960 |
| 51 | acetyl | cyclopentyl-methyloxy | " | " | 75-76 |
| 52 | hydrogen | 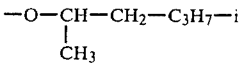 | " | " | 81 |
| 53 | " | —O—$CH(C_2H_5)_2$ | " | " | 80-82 |
| 54 | " | 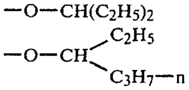 | " | " | oil, $n_D^{26}$ = 1.4982 |
| 55 | " | —O—CH(n-$C_3H_7)_2$ | " | " | 61 |
| 56 | " | —O—CH$(C_3H_7$—i$)_2$ | " | " | 82 |
| 57 | " | 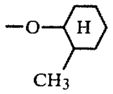 | " | " | 126-127 |
| 58 | acetyl | " | " | " | |
| 59 | phenoxycarbonyl | " | " | " | |
| 60 | 3'-chlorophenoxy-carbonyl | " | " | " | |

-continued

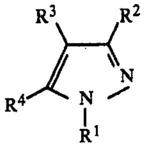

| No. | $R^1$ | $R^2$ | $R^3$ | $R^4$ | m.p. (°C.) |
|---|---|---|---|---|---|
| 61 | hydrogen | 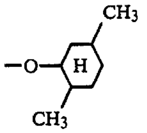 | " | " | 161 |
| 62 | acetyl | " | " | " | 85 |
| 63 | " | $-O-CH_2-C_3H_7-i$ | " | " | 82 |
| 64 | hydrogen | 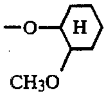 | " | " | 30° C., amorphous |
| 65 | acetyl | 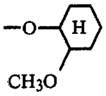 | " | " | oil, $n_D^{23} = 1.5113$ |
| 66 | hydrogen | $-O-CH_2-C_4H_9-tert.$ | " | " | 66-68 |
| 67 | acetyl | $-O-CH_2-C_4H_9-tert.$ | " | " | 98-99 |
| 68 | phenoxy-carboxyl | $-O-CH_2-C_4H_9-tert.$ | " | " | 128-129 |
| 69 | hydrogen | $-O-CH_2-CH-C_2H_5$<br>$CH_3$ | " | " | 46 |
| 70 | " | $-O-CH_2-CH(C_2H_5)_2$ | " | " | 47-48 |
| 71 | " | $-O-CH_2-CH-CH_2C_3H_7-i$<br>$CH_3$ | " | " | $n_D^{25} = 1.5469$ |
| 72 | " | 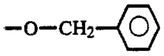 | " | " | |
| 73 | " | 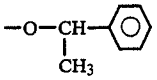 | " | " | |
| 74 | " | 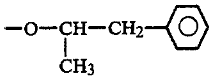 | " | " | $n_D^{27} = 1.5459$ |
| 75 | " | 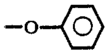 | " | " | 109-110 |
| 76 | acetyl | " | " | " | 68-70 |
| 77 | phenoxy-carbonyl | " | " | " | |
| 78 | hydrogen | 2'-methylphenoxy | " | " | 123 |
| 79 | acetyl | " | " | " | 91 |
| 80 | phenoxycarbonyl | " | " | " | |
| 81 | hydrogen | 2',3'-dimethyl-phenoxy | " | " | 150 |
| 82 | hydrogen | 2',4'-dimethyl-phenoxy | " | " | 161-163 |
| 83 | acetyl | 2',4'-dimethyl-phenoxy | " | " | 81-82 |
| 84 | hydrogen | 2',5'-dimethyl-phenoxy | " | " | 100-102 |
| 85 | acetyl | 2',5'-dimethyl-phenoxy | " | " | 109-110 |
| 86 | hydrogen | 3'-methyl-4'-chloro-phenoxy | " | " | 148 |
| 87 | " | 2'-methyl-4'-chloro-phenoxy | " | " | 146-147 |
| 88 | " | 4'-methylphenoxy | " | " | 137-139 |
| 89 | " | 4'-chlorophenoxy | " | " | 106 |
| 90 | " | 3'-methoxyphenoxy | " | " | 109 |
| 91 | acetyl | " | " | " | 70-71 |
| 92 | hydrogen | 3'-isopropylphenoxy | " | " | 72 |
| 93 | hydrogen | 3'-cyanophenoxy | " | " | |
| 94 | " | 3'-nitrophenoxy | " | " | |
| 95 | " | 4'-fluorophenoxy | " | " | |
| 96 | " | 3'-methoxycarbonyl-phenoxy | " | " | |

-continued
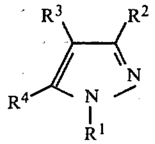
| No. | $R^1$ | $R^2$ | $R^3$ | $R^4$ | m.p. (°C.) |
|---|---|---|---|---|---|
| 97 | " | 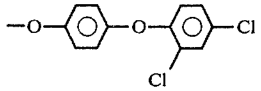 | " | " | |
| 98 | " | 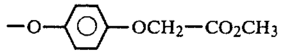 | " | " | |
| 99 | " | 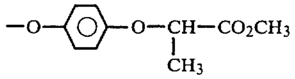 | " | " | |
| 100 | " | $-O-CH_2-CO_2CH_3$ | " | " | |
| 101 | " | $-O-CH(CH_3)-CO_2C_2H_5$ | " | " | |
| 102 | " | cyclopentyloxy | $-CO_2CH_3$ | $-CH_3$ | |
| 103 | " | cyclopentylthio | " | " | 92 |
| 104 | " | cyclooctyloxy | " | " | |
| 105 | " | cyclooctylthio | " | " | |
| 106 | " | cyclohexylthio | " | " | 113-114 |
| 107 | " | $-O-(CH_2)_2-OCH_3$ | " | " | |
| 108 | " | $-O-(CH_2)_2-CN$ | " | " | |
| 109 | " | $-O-(CH_2)_2-O-C(=O)-CH_3$ | " | " | |
| 110 | " | $-O-(CH_2)_2-S-CH_3$ | " | " | |
| 111 | " | 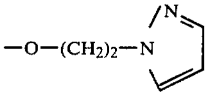 | " | " | |
| 112 | " | 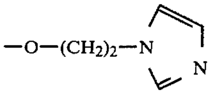 | " | " | |
| 113 | " | 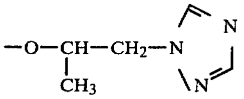 | " | " | |
| 114 | " | 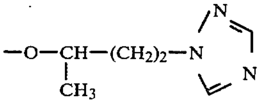 | " | " | |
| 115 | " | 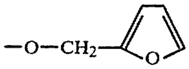 | " | " | |
| 116 | " | 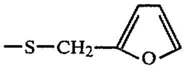 | " | " | 119-120 |
| 117 | " | 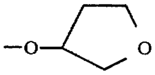 | " | " | |
| 118 | " | 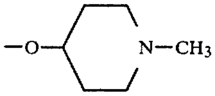 | " | " | |
| 119 | " | 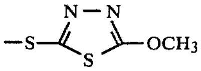 | " | " | |
| 120 | " | 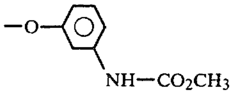 | " | " | |

-continued

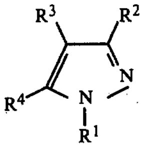

| No. | $R^1$ | $R^2$ | $R^3$ | $R^4$ | m.p. (°C.) |
|---|---|---|---|---|---|
| 121 | " | 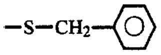 | " | " | 109-110 |
| 122 | " | 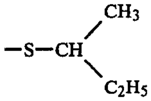 | " | " | 53 |
| 123 | " | $—S—CH_2—C_3H_7—i$ | " | " | 92-94 |
| 124 | " | $—S—(CH_2)_2—C_3H_7—i$ | " | " | 83-84 |
| 125 | " | $—S—CH—C_3H_7—n$<br>$CH_3$ | " | " | 54 |
| 126 | " | $—S—C_7H_{15}—n$ | " | " | 58-60 |
| 127 | " | $—S—C_8H_{17}—n$ | " | " | 54-55 |
| 128 | " | 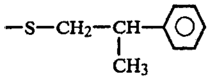 | " | " | 100-101 |
| 129 | " | $—S—(CH_2)_2—CH—(CH_2)_3—C_3H_7—i$<br>$CH_3$ | " | " | $n_D^{26} = 1.5195$ |
| 130 | " | $—S—CH_2—CO_2Et$ | " | " | |
| 131 | " | $—S—CH—CO_2CH_3$<br>$CH_3$ | " | " | |
| 132 | " | thiophenyl | " | " | 109-110 |
| 133 | " | 2'-methylphenylthio | " | " | |
| 134 | " | 3'-methylphenylthio | " | " | |
| 135 | " | 2'-methoxyphenylthio | " | " | |
| 136 | " | $—O—CH(OCH_3)_2$<br>$CH_3$ | $CO_2CH_3$ | $CH_3$ | |
| 137 | " | $—O—CH—C_4H_9—tert.$<br>$CH_3$ | " | " | 88-91 |
| 138 | " | $—OCH_2—C_3H_7—i$ | $—CO_2C_2H_5$ | " | |
| 139 | " | $—OCH_2—C_3H_7—i$ | $—CO_2C_3H_7i$ | " | |
| 140 | " | " | $—CO_2CH_2CH_2—Cl$ | " | |
| 141 | " | " | $—CO_2—C_2H_4—OCH_3$ | " | |
| 142 | " | " | 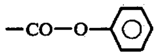 | " | |
| 143 | " | " | $—CO—SC_2H_5$ | " | |
| 144 | " | " | $—CO—CH_3$ | " | |
| 145 | " | 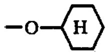 | " | " | |
| 146 | " | $—O—CH_2C_4H_9—tert.$ | " | " | |
| 147 | acetyl | $—O—CH_2C_4H_9—tert.$ | $—CO—CH_3$ | $—CH_3$ | |
| 148 | hydrogen | " | $—CO—OCH_2CF_3$ | " | |
| 149 | " | $O—C_4H_9—iso$ | 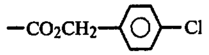 | methyl | |
| 150 | " | " | $—CO—O—C_2H_4—CN$ | " | |
| 151 | " | " | 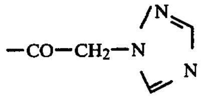 | " | |
| 152 | " | " | $—CONHCH_3$ | " | |
| 153 | " | " | $—CON(CH_3)_2$ | " | |
| 154 | " | " | Br | " | |
| 155 | " | " | CN | " | |
| 156 | H | $—O—C_4H_9—iso$ | $—CO—CF_3$ | " | |
| 157 | " | " | $—CO_2CH_3$ | $C_2H_5$ | |
| 158 | " | " | " | $—C_3H_7—i$ | |
| 159 | " | " | " | 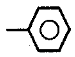 | |
| 160 | " | " | $—CO_2CH_3$ | $—C_4H_9—tert.$ | |
| 161 | " | " | hydrogen | | |
| 162 | acetyl | " | " | " | |

-continued

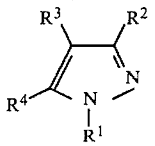

| No. | $R^1$ | $R^2$ | $R^3$ | $R^4$ | m.p. (°C.) |
|---|---|---|---|---|---|
| 163 | phenoxycarbonyl | " | " | " | |
| 164 | hydrogen | " | " | methoxy | |
| 165 | " | " | " | chlorine | |
| 166 | " | " | " | $-CF_3$ | |
| 167 | " | " | " | $-CO_2CH_3$ | |
| 168 | acetyl | $-O-CH_2-CH-C_2H_5$<br>$CH_3$ | " | $-CH_3$ | 46 |
| 169 | " | 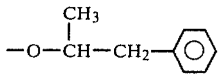 | " | " | $n_D^{25} = 1.5412$ |
| 170 | " | $-O-CH(C_2H_5)_2$ | " | " | 41 |
| 171 | hydrogen | $-S-(CH_2)_2-OCH_3$ | " | " | 70-73 |
| 172 | acetyl | thiobenzyl | " | " | 92 |
| 173 | phenoxycarbonyl | " | " | " | 105-107 |
| 174 | acetyl | $-S-C_7H_{15}-n$ | " | " | 55-57 |
| 175 | " | $-S-C_8H_{17}-n$ | " | " | 38-40 |
| 176 | " | $-O-CH_2-CH-CH_2-C_3H_7-i$<br>$CH_3$ | " | " | $n_D^{26} = 1.4875$ |
| 177 | " | 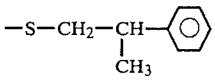 | " | " | 67-68 |
| 178 | hydrogen | $-O-C_3H_7i$ | $-CO_2C_2H_5$ | " | 79-80 |
| 179 | phenoxycarbonyl | $-S-CH_2-C_3H_7-i$ | $-CO_2CH_3$ | " | 95-96 |
| 180 | hydrogen | $O-CH_2-CH-CH_2-C_3H_7-i$<br>$C_2H_5$ | " | " | $n_D^{26} = 1.4912$ |
| 181 | acetyl | thiophenyl | $CO_2CH_3$ | " | 86-88 |
| 182 | " | $-S-C_4H_9-sec.$ | $CO_2CH_3$ | $CH_3$ | 76-78 |
| 183 | " | 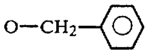 | $CO_2CH_3$ | " | |
| 184 | " | " | 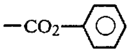 | " | |
| 185 | hydrogen | " | " | " | |
| 186 | phenoxycarbonyl | " | $CO_2CH_3$ | " | |
| 187 | " | thiophenyl | " | " | 119-121 |
| 188 | " | $-O-CH_2-CH(C_2H_5)_2$ | " | " | 87-88 |
| 189 | " | $-O-C_3H_7-i$ | " | " | 75-77 |
| 190 | " | 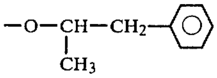 | " | " | 74-75 |
| 191 | " | 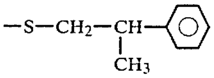 | " | " | 90-91 |
| 192 | hydrogen | $-O-CH_2-CH-C_3H_7-i$<br>$CH_3$ | " | " | $n_D^{27} = 1.4902$ |
| 193 | acetyl | " | " | " | 72-73 |
| 194 | phenoxycarbonyl | $-S-(CH_2)_2-CH-(CH_2)_3-C_3H_7-i$<br>$CH_3$ | " | " | $n_D^{30} = 1.5318$ |
| 195 | methoxycarbonyl | $-S-C_3H_7-i$ | " | " | 87-88 |
| 196 | 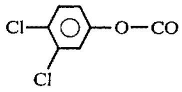 | 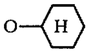 | $-CO_2CH_3$ | $-CH_3$ | 106-108 |
| 197 | 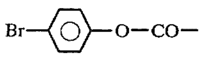 | " | " | " | 61-63 |
| 198 | 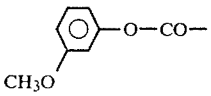 | " | " | " | 124 |

-continued
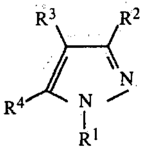
| No. | $R^1$ | $R^2$ | $R^3$ | $R^4$ | m.p. (°C.) |
|---|---|---|---|---|---|
| 199 | $HC{\equiv}C-CH_2-O-CO-$ | $-O-C_4H_9-iso$ | " | " | |
| 200 | $n\text{-}C_3H_7-O-CO-$ | " | " | " | |
| 201 | $n\text{-}C_4H_9-O-CO-$ | " | " | " | 51 |
| 202 | $CH_3O-(CH_2)_2-O-CO-$ | " | " | " | 59 |
| 203 | $Cl-(CH_2)_2-O-CO-$ | " | " | " | 63-64 |
| 204 | $CH_3-S-CO-$ | " | " | " | $n_D^{26} = 1.5260$ |
| 205 | $n\text{-}C_3H_7-S-CO-$ | " | " | " | $n_D^{26} = 1.5171$ |
| 206 | tert. $C_4H_9-O-CO-$ | " | " | " | |
| 207 | tert. $C_4H_9-S-CO-$ | " | " | " | |
| 208 | 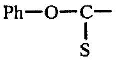 | " | " | " | |
| 209 | 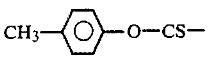 | " | " | " | |
| 210 | $Ph-S-CO-$ | " | " | " | |
| 211 | 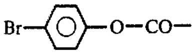 | " | " | " | 142 |
| 212 | 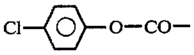 | " | " | " | 75 |
| 213 | 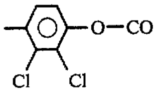 | 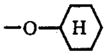 | " | " | 112-113 |
| 214 | 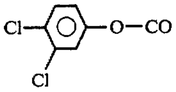 | $-O-C_4H_9-iso$ | " | " | 96-97 |
| 215 | H . HCl | 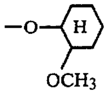 | " | " | 157-158 |
| 216 | 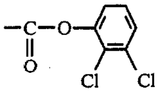 | 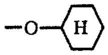 | " | " | 112-113 |
| 217 | 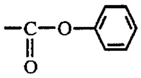 | 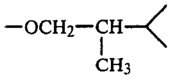 | " | " | 84 |
| 218 | 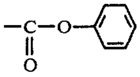 | 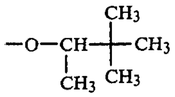 | " | " | 86-88 |
| 219 | 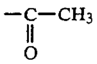 | 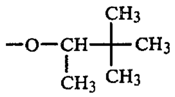 | " | " | 102-103 |
| 220 | H | 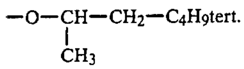 | " | " | 157-158 |
| 221 | 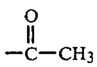 | 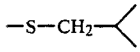 | " | " | 40-41 |
| 222 | $-CHO$ | 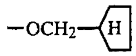 | " | " | 105-106 |
| 223 | 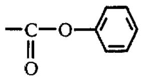 | 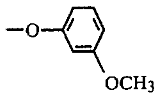 | " | " | 105-107 |
| 224 | 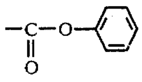 | 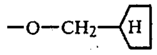 | " | " | 89 |

-continued

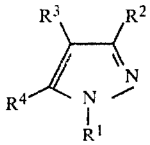

| No. | $R^1$ | $R^2$ | $R^3$ | $R^4$ | m.p. (°C.) |
|---|---|---|---|---|---|
| 225 | H | 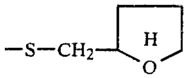 | " | " | 139-141 |
| 226 | H | $-S-CH_2-\underset{\underset{CH_3}{\mid}}{CH}-COOCH_3$ | " | " | 71-74 |
| 227 | H | $-S-\underset{\underset{CH_3}{\mid}}{CH}-CH_2-COOC_2H_5$ | " | " | 52-53 |
| 228 | 3'-chlorophenoxy-carbonyl | $O-\underset{\underset{CH_3}{\mid}}{CH}-C_4H_9$tert. | " | " | 110 |
| 229 | 2'-chloro-4'-nitro-phenoxycarbonyl | $O-CH_2-C_3H_7-i$ | " | " | 81 |
| 230 | 2',4',5'-trichloro-phenoxycarboxyl | 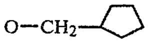 | " | " | 79-82 |
| 231 | 2',4',5'-trichloro-phenoxycarbonyl | $-O-CH_2-C_3H_7-i$ | " | " | 70-72 |
| 232 | 2'-sec.-$C_4H_9$—phenoxy-carbonyl | $O-CH_2-C_4H_9-$tert. | " | " | $n_D^{20} = 1.5063$ |
| 233 | 2'-ethylphenoxy-carbonyl | 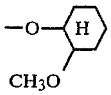 | " | " | oil |
| 234 | 2'-ethylphenoxy-carbonyl | 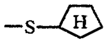 | " | " | 90-92 |
| 235 | 2'-chloro-4', 5'-dimethyl-phenoxycarbonyl | $O-CH_2-C_3H_7-i$ | " | " | 125-127 |
| 236 | 4'-sec-butyl-phenoxycarbonyl | 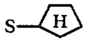 | " | " | oil |
| 237 | 2'-sec-butyl-phenoxycarbonyl | $S-CH_2-C_3H_7-i$ | " | " | oil |
| 238 | 2',3',5',6'-tetra-methylphenoxy-carbonyl | $O-C_3H_7i$ | " | " | 142-145 |
| 239 | 2'-chloro-4'-nitro-phenoxycarbonyl | $O-C_4H_9-$sec. | " | " | 97-98 |
| 240 | H | 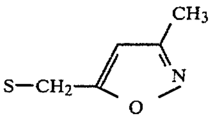 | " | " | 148-149 |
| 241 | H | 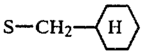 | " | " | 111-113 |
| 242 | $CH_3-CO$ | " | " | " | 53 |
| 243 | H | 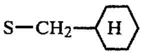 | " | " | 127-128 |
| 244 | $CH_3-CO$ | " | " | " | 59-60 |
| 245 | $CH_3CO-$ | 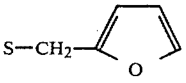 | " | " | |
| 246 | $CH_3-CO$ | 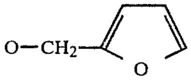 | " | " | |
| 247 | H | $S-C_4H_9$tert. | " | " | 96-98 |
| 248 | H | 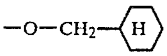 | $COOCH_3$ | " | 87-89 |
| 249 | $-\underset{\underset{O}{\Vert}}{C}-CH_3$ | " | " | " | 99-100 |

The active ingredients according to the invention may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion con-centrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

EXAMPLE 5

90 parts by weight of compound 1 is mixed with 10 parts by weight of N-methyl-α-pyrrolidone. A mixture is obtained which is suitable for application in the form of very fine drops.

EXAMPLE 6

20 parts by weight of compound 2 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 7

20 parts by weight of compound 3 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and finely distributing it therein, an aqueous dispersion is obtained containing 0.02% by weight of the active ingredient.

EXAMPLE 8

20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 9

20 parts by weight of compound 2 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

EXAMPLE 10

3 parts by weight of compound 3 is intimately mixed with 97 parts by weight of particulate kaolin. A dust is obtained containing 3% by weight of the active ingredient.

EXAMPLE 11

30 parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 12

40 parts by weight of compound 1 is intimately mixed with 10 parts of the sodium salt of a phenolsulfonic acid-urea-formaldehyde condensate, 2 parts of silica gel and 48 parts of water. Dilution in 100,000 parts by weight of water gives an aqueous dispersion containing 0.04 wt% of active ingredient.

EXAMPLE 13

20 parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The new compounds are herbicidally effective, and are suitable for removing or suppressing unwanted plant growth in crops or on uncultivated land. It goes of course without saying that the intensity of action varies from compound to compound, or the action of the compounds on unwanted plants or crop plants varies. The influence of the compounds on unwanted plants is shown in the following tables, which contain results from greenhouse experiments.

The vessels employed were plastic flowerpots having a volume of 300 $cm^3$, and which were filled with a sandy loam containing about 1.5% humus. The seeds of the test plants (cf. Table 1) were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals, and prevented readily volatile active ingredients from evaporating.

For postemergence treatment, the plants were first grown to a height of 3 to 10 cm, depending on the growth shape, before being treated. The vessels were not covered after treatment. The pots were set up in the greenhouse-species from warmer areas at from 25° to 40° C., and species from moderate climates at 15° to 30° C. The experiments were run for from 4 to 6 weeks. During this period, the plants were tended and their reactions to the various treatments assessed. The following tables contain the compounds investigated, the application rates in kg/ha of active ingredient, and the plants used for the tests. The scale used for assessment was 0 to 100, 0 denoting no damage or normal emergence, and 100 denoting nonemergence or complete destruction of at least the visible plant parts.

RESULTS

The new pyrazole(thio)-ether derivatives exhibit interesting herbicidal properties in both pre- and postemergence use. They act on both broadleaved and grassy unwanted plants, and cause no damage to certain crop plants although they come into direct contact with the active ingredients. The compounds are used in the main after emergence of the unwanted plants, regardless of whether crop plants are growing on the treated areas or not.

If the crop plants tolerate the active ingredients less well, application techniques may be used in which the agents are sprayed from suitable equipment in such a manner that the leaves of sensitive crop plants are if possible not touched, and the agents reach the soil or the unwanted plants growing beneath the crop plants (post-directed, lay-by treatment).

The broad range of combatable species from the most widely varying botanical families also makes the agents suitable for removing unwanted grass and weeds from tree and bush plantations and sugarcane.

The active ingredients may also be used on non-crop areas such as railroad track and industrial units, parking lots, storage spaces, pathways, edges of ditches, and cut- over land. Whether the plants are completely eliminated or their growth is merely suppressed and kept under control without killing them is a question of dosage amounts.

Some of the compounds are also suitable as desiccants for green leaves and stems. Such agents are used for instance for killing off potato tops before the potatoes are mechanically harvested; for combating weeds in ripe cereal fields prior to harvesting; for accelerating drying in soybeans before combine harvesting; and for removing green plant parts in cotton ready for picking.

In view of the many application methods possible, the agents according to the invention, or mixtures containing them, may be used not only on the crop plants listed in the tables, but also in a much larger range of crops for removing unwanted plants. Depending on the object to be achieved, the application rates vary from 0.1 to 15 kg/ha and more.

The following crop plants may be mentioned by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp.*rapa* | fodder beets |
| *Beta vulgaris* spp. *esculenta* | table beets, red beets |
| *Brassica napus var. napus* | rape |
| *Brassica napus var. napohrassica* | |
| *Brassica napus var. rapa* | turnips |
| *Brassica rapas var. silvestris* | |
| *Camellia sinensis* | tea plants |
| *Carthamus tinctorius* | safflower |
| *Citrus limon* | lemons |
| *Citrus maxima* | grapefruits |
| *Citrus reticulata* | |
| *Citrus sinensis* | orange trees |
| *Coffea arabica (Coffea canephora, Coffea liberica)* | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum (Gossypium arboreum Gossypium herbaceum Gossypium vitifolium)* | cotton |
| *Helianthus annus* | sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |

-continued

| Botanical name | Common name |
|---|---|
| *Medicago sativa* | alfalfa (lucerne) |
| *Mentha piperita* | peppermint |
| *Musa* spp. | banana plants |
| *Nicothiana tabacum* (*N. rustica*) | tobacco |
| *Olea europaea* | olive trees |
| *Oryza sativa* | rice |
| *Panicum miliaceum* | |
| *Phaseolus lunatus* | limabeans |
| *Phaseolus mungo* | mungbeans |
| *Phaseolus vulgaris* | snapbeans, green beans, dry beans |
| *Pennisetum glaucum* | |
| *Petroselinum crispum* spp. *tuberosum* | parsley |
| *Picea abies* | Norway spruce |
| *Pinus* spp. | pine trees |
| *Pisum sativum* | English peas |
| *Prunus avium* | cherry trees |
| *Prunus domestica* | plum trees |
| *Prunus persica* | peach trees |
| *Pyrus communis* | pear trees |
| *Ribes sylvestre* | redcurrants |
| *Ribes uva-crispa* | |
| *Ricinus communis* | |
| *Saccharum officinarum* | sugar cane |
| *Secale cereale* | rye |
| *Sesamum indicum* | sesame |
| *Solanum tuberosum* | Irish potatoes |
| *Sorghum bicolor (s. vulgare)* | grain sorghum |
| *Sorghum dochna* | |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinensis* (*V. unguiculata*) | cow peas |
| *Vitis vinifera* | grapes |
| *Zea mays* | Indian corn, sweet corn, maize |

The compounds according to the invention may also be mixed or combined with numerous other herbicides or growth-regulating compounds in order to further extend the spectrum of action, to achieve synergistic effects, or to improve persistence in the soil. Depending on the area treated and the objective, the following compounds, or similar derivatives, may be admixed:

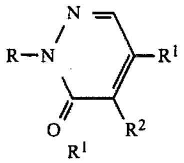

| R | $R^1$ | $R^2$ |
|---|---|---|
| 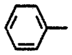 | $NH_2$ | Cl |
| 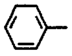 | $NH_2$ | Br |
| 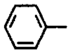 | $OCH_3$ | $OCH_3$ |
| 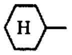 | $OCH_3$ | $OCH_3$ |
| 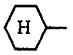 | $NH_2$ | Cl |

-continued

| | | |
|---|---|---|
| 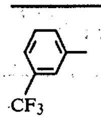 | $NHCH_3$ | Cl |
| 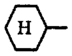 | $NH_2$ | Br |
| 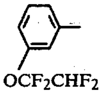 | $NH . CH_3$ | Cl |

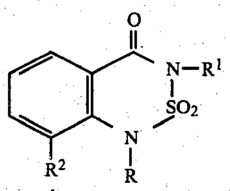

| R | $R^1$ | $R^2$ | |
|---|---|---|---|
| H | 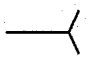 | H | (salts) |
| H | 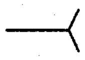 | $CH_3$ | " |
| H | 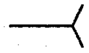 | Cl | " |
| H | 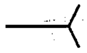 | F | " |
| $CH_2OCH_3$ | 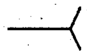 | F | |
| $CH_2OCH_3$ | 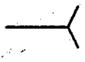 | H | |
| CN | 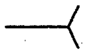 | H | |
| CN | 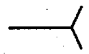 | Cl | |
| CN | 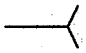 | F | |
| $CH_2N_3$ | 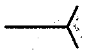 | H | |

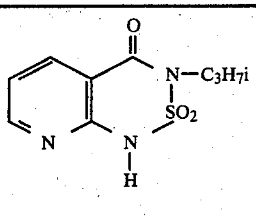

(salts)

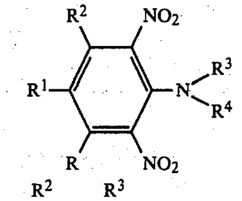

| R | $R^1$ | $R^2$ | $R^3$ | $R^4$ |
|---|---|---|---|---|
| H | $F_3C$ | H | $C_2H_5$ | $C_4H_9$ |
| H | $F_3C$ | H | $n . C_3H_7$ | $n . C_3H_7$ |
| H | $F_3C$ | H | $-CH_2-CH_2Cl$ | $n . C_3H_7$ |
| H | $SO_2NH_2$ | H | $n . C_3H_7$ | $n . C_3H_7$ |
| H | $F_3C$ | H | $nC_3H_7$ | 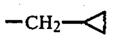 |

-continued

| | | | | |
|---|---|---|---|---|
| $H_3C$ | $H_3C$ | H | H | 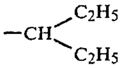 |

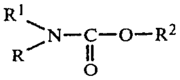

| R | $R^1$ | $R^2$ |
|---|---|---|
| 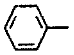 | H | $iC_3H_7$ |
| $CH_3$ | H | 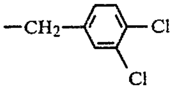 |
| 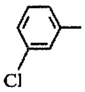 | H | 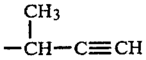 |
| 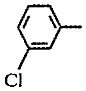 | H | $iC_3H_7$ |
| 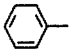 | H | 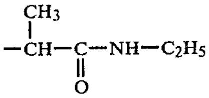 |
| 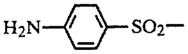 | H | $CH_3$ |

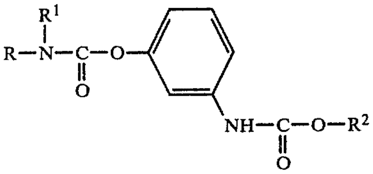

| | | |
|---|---|---|
| 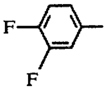 | H | $C_2H_5$ |
| 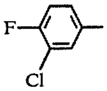 | H | $C_2H_5$ |
| 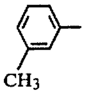 | H | $CH_3$ |
| 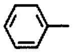 | H | $C_2H_5$ |
| 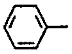 | $CH_3$ | $CH_3$ |
| 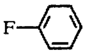 | H | $CH_3$ |

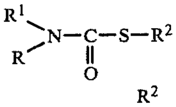

| R | $R^1$ | $R^2$ |
|---|---|---|
| $iC_3H_7$ | $iC_3H_7$ | $CH_2-CCl=CCl_2$ |
| $iC_3H_7$ | $iC_3H_7$ | $CH_2-CCl=CHCl$ |
| n . $C_3H_7$ | n . $C_3H_7$ | $C_2H_5$ |

-continued

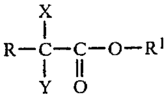

| R | X | Y | $R^1$ |
|---|---|---|---|
| $CH_3$ | Cl | Cl | Na |
| Cl | Cl | Cl | Na |
| 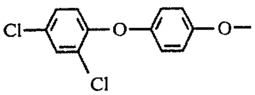 | H | $CH_3$ | $CH_3$ |
| 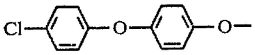 | H | $CH_3$ | 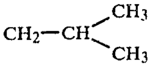 |
| 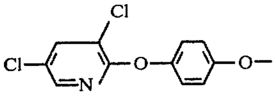 | H | $CH_3$ | Na |
| 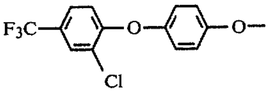 | H | $CH_3$ | Na |
| 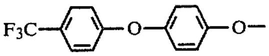 | H | $CH_3$ | $CH_3$ |

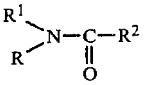

| R | $R^1$ | $R^2$ |
|---|---|---|
| 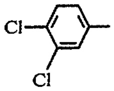 | H | 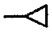 |
| 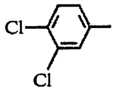 | H | $C_2H_5$ |
| 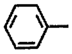 | 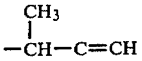 | $CH_2Cl$ |
| 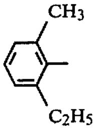 | 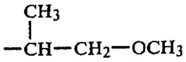 | $CH_2Cl$ |
| 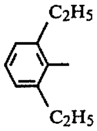 | $-CH_2OCH_3$ | $CH_2Cl$ |
| 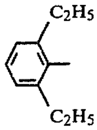 | 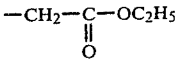 | $CH_2Cl$ |
| 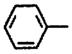 | $iC_3H_7$ | $CH_2Cl$ |
| 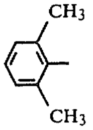 | $-CH_2-CH_2-OCH_3$ | $Cl_2Cl$ |
| $C_2H_5$ | $C_2H_5$ | 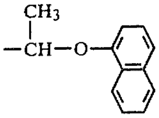 |

-continued

| | | |
|---|---|---|
| 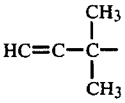 | H | 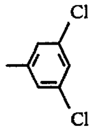 |
| 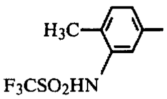 | H | $CH_3$ |
| 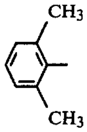 | 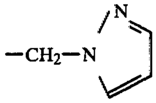 | $CH_2Cl$ |
| 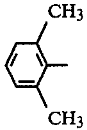 | 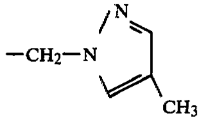 | $CH_2Cl$ |
| 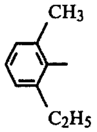 | 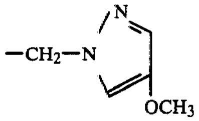 | $CH_2Cl$ |
| 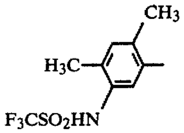 | H | $CH_3$ |
| 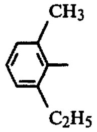 | 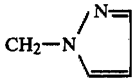 | $CH_2Cl$ |
| 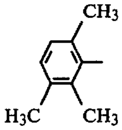 | 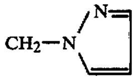 | $CH_2Cl$ |
| 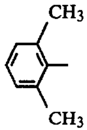 | 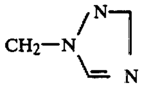 | $CH_2Cl$ |

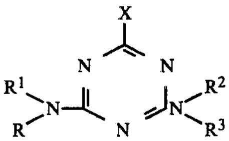

| R | $R^1$ | X | $R^2$ | $R^3$ |
|---|---|---|---|---|
| H | $C_2H_5$ | $SCH_3$ | H | $C_2H_5$ |
| H | $iC_3H_7$ | $SCH_3$ | H | $C_2H_5$ |
| H | $iC_3H_7$ | Cl | H | $C_2H_5$ |
| H | $iC_3H_7$ | Cl | H | 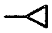 |
| H | $C_2H_5$ | Cl | H | $C_2H_5$ |
| H | $C_2H_5$ | Cl | H | 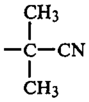 |
| H | $iC_3H_7$ | $OCH_3$ | H | $iC_3H_7$ |

-continued

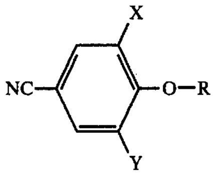

| X | Y | R |
|---|---|---|
| Br | Br | H (salts) |
| I | I | H (salts) |
| Br | Br | 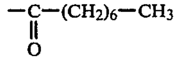 |

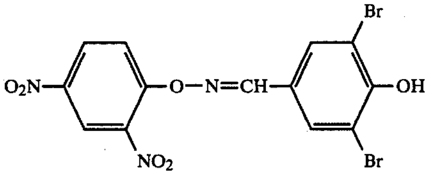 salts, esters

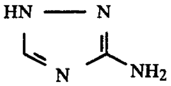

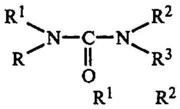

| R | $R^1$ | $R^2$ | $R^3$ |
|---|---|---|---|
| 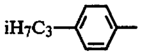 | H | $CH_3$ | $CH_3$ |
| 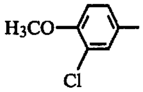 | H | $CH_3$ | $CH_3$ |
| 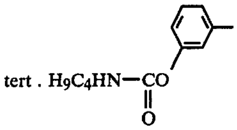 | H | $CH_3$ | $CH_3$ |
| 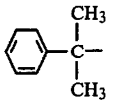 | H | H | 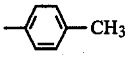 |
| 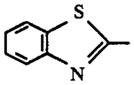 | $CH_3$ | $CH_3$ | H |
| 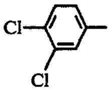 | H | $CH_3$ | $CH_3$ |
| 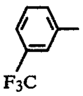 | H | $CH_3$ | $CH_3$ |
| 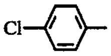 | H | $CH_3$ | 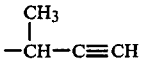 |
| 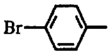 | H | $CH_3$ | $OCH_3$ |
| 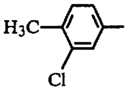 | H | $CH_3$ | $CH_3$ |
| 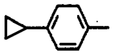 | H | $CH_3$ | $CH_3$ |

-continued
| | | | |
|---|---|---|---|
| 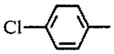 | H | $CH_3$ | $OCH_3$ |
| 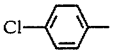 | H | $CH_3$ | $CH_3$ |
| 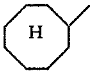 | H | $CH_3$ | $CH_3$ |
| 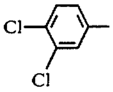 | H | $CH_3$ | $OCH_3$ |
| 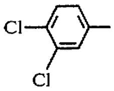 | H | $CH_3$ | H |
| 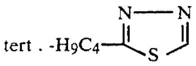 | $CH_3$ | $CH_3$ | H |
| 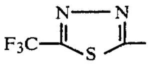 | $CH_3$ | $CH_3$ | H |
| 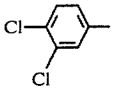 | H | $C_2H_5$ | $C_2H_5$ |
| 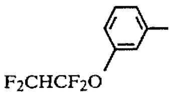 | H | $CH_3$ | $CH_3$ |
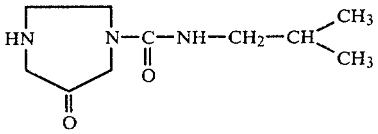
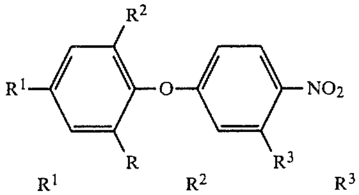
| R | $R^1$ | $R^2$ | $R^3$ |
|---|---|---|---|
| Cl | $CF_3$ | H | COOH salts |
| Cl | Cl | H | H |
| Cl | Cl | H | 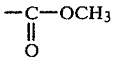 |
| H | $CF_3$ | Cl | $OC_2H_5$ |
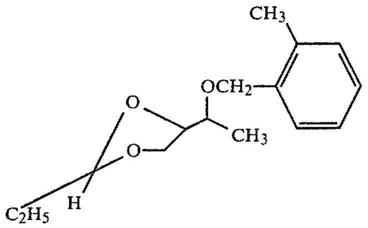
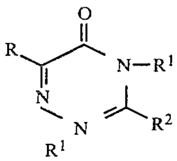
| R | $R^1$ | $R^2$ |
|---|---|---|
| tert.-$C_4H_9$ | $NH_2$ | $SCH_3$ |
-continued
| | | |
|---|---|---|
| 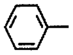 | $NH_2$ | $CH_3$ |
| 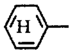 | $NH_2$ | $SCH_3$ |
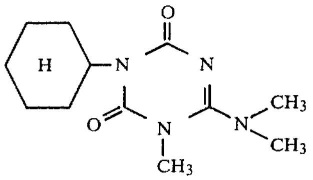
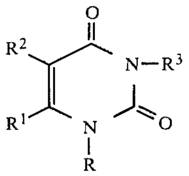
| R | $R^1$ | $R^2$ | $R^3$ |
|---|---|---|---|
| H | $CH_3$ | Br | 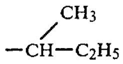 |
| H | $CH_3$ | Br | $iC_3C_7$ |
| H | $CH_3$ | Cl | tert.-$C_4H_9$ |
| H | $CH_3$ | Cl | 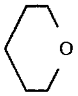 |
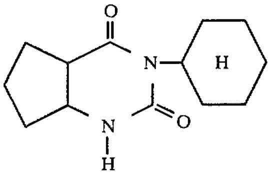
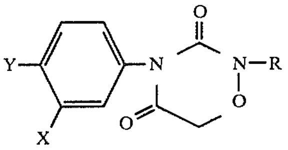
| X | Y | R |
|---|---|---|
| $CF_3$ | H | $CH_3$ |
| H | F | $CH_3$ |
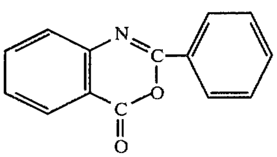
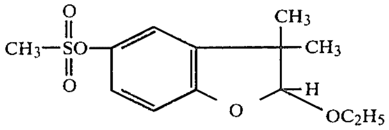

-continued

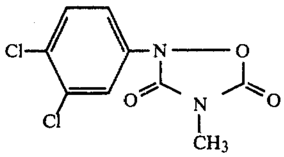

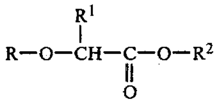

| R | $R^1$ | $R^2$ | |
|---|---|---|---|
| 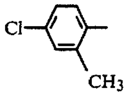 | $CH_3$ | H | salts, esters, amides |
| 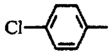 | H | H | salts, esters, amides |

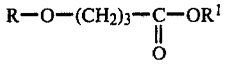

| R | $R^1$ | |
|---|---|---|
| 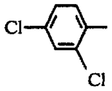 | H | salts, esters, amides |
| 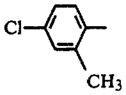 | H | salts, esters, amides |

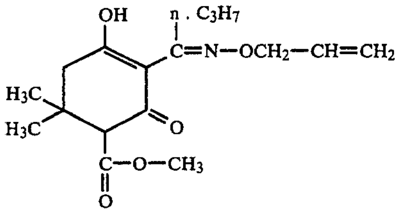

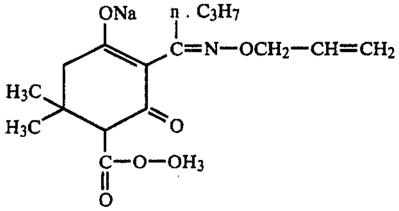

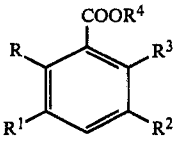

| R | $R^1$ | $R^2$ | $R^3$ | $R^4$ | |
|---|---|---|---|---|---|
| H | Cl | $NH_2$ | Cl | H | salts, esters, amides |
| Cl | Cl | H | Cl | Na | |
| Cl | H | Cl | $OCH_3$ | H | salts, esters, amides |
| Cl | Cl | H | Cl | | H . $(CH_3)_2NH$ |

-continued

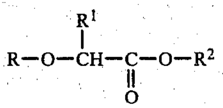

| R | $R^1$ | $R^2$ | |
|---|---|---|---|
| 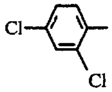 | $CH_3$ | H | salts, esters, amides |
| 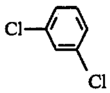 | H | H | salts, esters, amides |
| 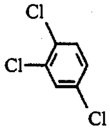 | H | H | salts, esters, amides |
| 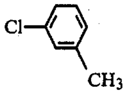 | H | H | salts, esters, amides |
| 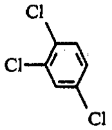 | $CH_3$ | H | salts, esters, amides |

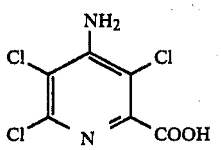

salts, esters

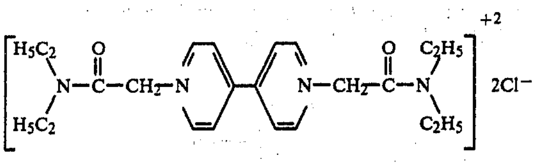

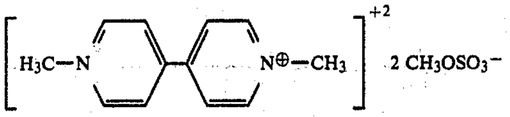

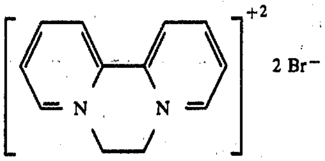

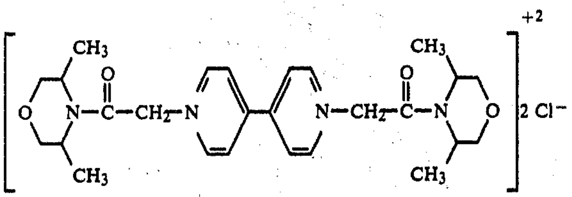

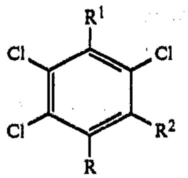

-continued
| R | $R^1$ | $R^2$ |
|---|---|---|
| $COOCH_3$ | $COOCH_3$ | Cl |
| 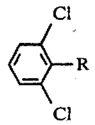 | R = CN<br>R = $CSNH_2$ | |
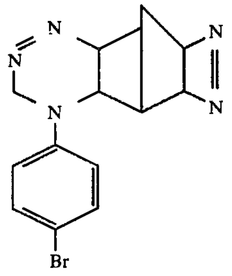
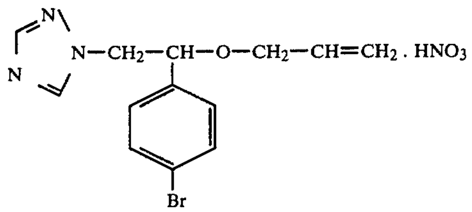
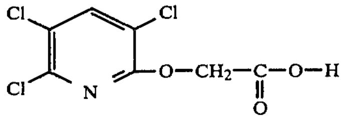 salts, esters, amides
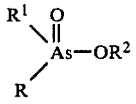
| R | $R^1$ | $R^2$ |
|---|---|---|
| OH | $CH_3$ | Na |
| $CH_3$ | $CH_3$ | Na |
| $CH_3$ | $CH_3$ | OH |
| ONa | $CH_3$ | Na |
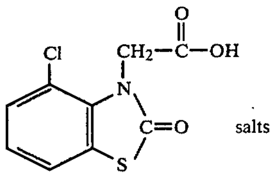 salts
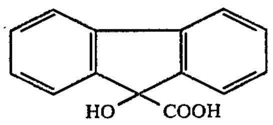 salts, esters
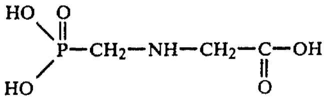 (salts)
-continued
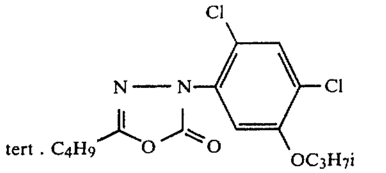
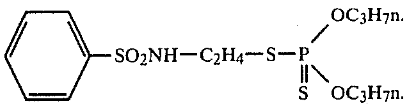
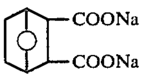 and other salts
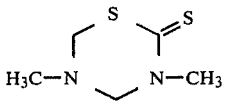
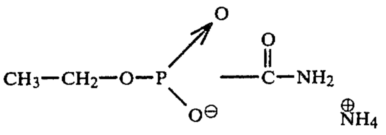
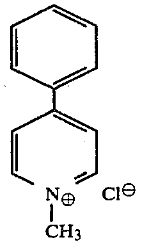
$NH_4SCN$
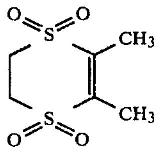
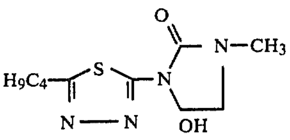
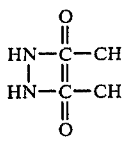 (salts)
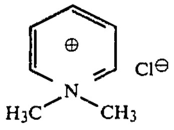

-continued

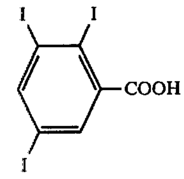

salts, esters, amides

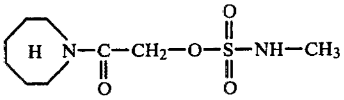

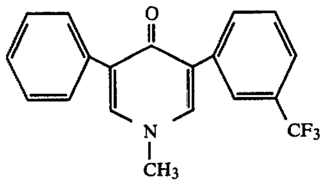

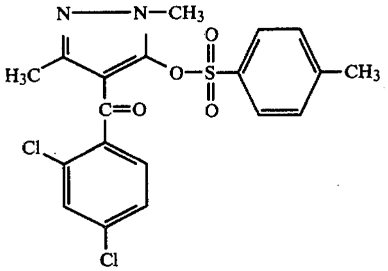

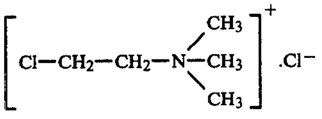

-continued

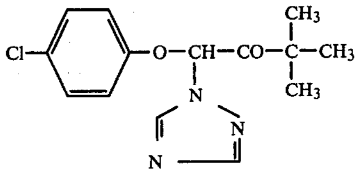

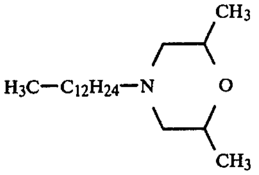

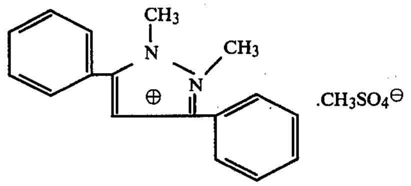

It may also be useful to apply the new compounds, either alone or in combination with other herbicides, in admixture with other crop protection agents, e.g., agents for combating pests or phytopathogenic fungi or bacteria. The compounds may also be mixed with solutions of mineral matters used to remedy nutritional or trace element deficiencies.

Under certain circumstances, it may also be advantageous to apply the agents, either alone or in the above combinations, in admixture with commercially available solid or liquid mineral fertilizers.

TABLE 1

List of plant names

| Botanical name | Abbreviation in tables | Common name |
|---|---|---|
| *Abutilon theophrasti* | *Abut. theo.* | velvet leaf |
| *Amaranthus retroflexus* | *Amar. ret.* | redroot pigweed |
| *Arachys hypogaea* | *Arachys hyp.* | peanuts (groundnuts) |
| *Avena fatua* | *Avena fatua* | wild oats |
| *Centaurea cyanus* | *Centaurea cyanus* | cornflower |
| *Chenopodium album* | *Chenopodium album* | lambsquarters |
| *Chrysanthemum segetum* | *Chrys. seg.* | corn marigold |
| *Echinochloa crus galli* | *Echin. c. g.* | barnyardgrass |
| *Eleusine indica* | *Eleus. ind.* | goosegrass |
| *Euphorbia geniculata* | *Euph. genic.* | South American member of the spurge family |
| *Ipomoea* spp. | *Ipomoea* spp. | morningglory |
| *Lolium multiflorum* | *Lolium mult.* | annual ryegrass |
| *Sesbania exaltata* | *Sesbania exaltata* | hemp sesbania (coffeeweed) |
| *Sinapis alba* | *Sinapis alba* | white mustard |
| *Sorghum bicolor* | *Sorghum bicolor* | sorghum |
| *Stellaria media* | *Stellaria media* | chickweed |
| *Triticum aestivum* | *Triticum aestivum* | wheat |
| *Zea mays* | *Mais* | Indian corn |
| *Lamium amplexicaule* | *Lamium amplex.* | henbit |
| *Lamium* spp. | *Lamium* spp. | dead nettle |
| *Solanum nigrum* | *Solanum nigrum* | black nightshade |
| *Gossypium hirsutum* | *Gossypium hirsutum* | cotton |

TABLE 2

Selective control of *Avena fatua* and other weeds in wheat; postemergence treatment in the greenhouse

| Compound no. | kg/ha | Test plants and % damage *Triticum aestivum* | *Avena fatua* | *Chenopodium album* | *Stellaria media* |
|---|---|---|---|---|---|
| 90 | 0.5 | 0 | 80 | 98 | 95 |
| | 1.0 | — | 100 | 98 | 100 |
| | 2.0 | 0 | 100 | — | 100 |
| 49 | 0.5 | 0 | 80 | 98 | 100 |
| | 1.0 | — | 85 | 98 | 100 |
| | 2.0 | 0 | 100 | — | 100 |
| 51 | 0.5 | 0 | 50 | 98 | 100 |
| | 1.0 | — | 95 | 98 | 100 |
| | 2.0 | 0 | 95 | — | 100 |
| 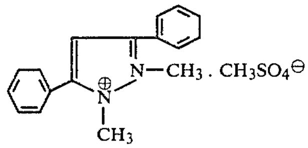 prior art | 0.5 | 6 | 33 | — | 18 |
| | 1.0 | 16 | 56 | — | 20 |
| | 2.0 | 28 | 72 | — | 35 |

0 = no damage, 100 = plants withered

TABLE 3

Selective control of unwanted plants in groundnuts; postemergence treatment in the greenhouse

| Compound no. | kg/ha | Test plants and % damage *Arachys hyp.* | *Amar. ret.* | *Abut. theo.* | *Chrys. seg.* | *Echin. c.g.* | *Eleu. ind.* | *Euph. genic.* | Ipomoea spp. | *Sesbania exaltata* |
|---|---|---|---|---|---|---|---|---|---|---|
| 40 | 0.5 | 5 | 100 | 100 | 100 | 100 | 98 | 100 | 92 | 100 |
| | 1.0 | 5 | 100 | 100 | 100 | 100 | 100 | 100 | 92 | 100 |
| | 2.0 | 10 | 100 | — | 100 | 100 | — | 100 | 100 | 100 |
| 57 | 0.5 | 0 | 100 | 100 | — | 100 | 80 | 100 | 100 | 100 |
| | 1.0 | 0 | 100 | 100 | — | 100 | 95 | 100 | 100 | 100 |
| | 2.0 | 100 | — | — | 100 | — | 100 | 100 | 100 | |
| 64 | 0.5 | 0 | — | — | — | 92 | — | — | 72 | 100 |
| | 1.0 | 0 | 90 | — | — | 100 | — | — | 72 | 100 |
| | 2.0 | 0 | — | — | — | 100 | — | — | 100 | — |
| 76 | 0.5 | 0 | 100 | 100 | 100 | 100 | 100 | 98 | 75 | 100 |
| | 1.0 | 2 | 100 | 100 | 100 | 100 | 100 | 100 | 75 | 100 |
| | 2.0 | 10 | 100 | — | 100 | 100 | — | 100 | 100 | 100 |
| 44 | 0.5 | 5 | 50 | 100 | 100 | 90 | 100 | 100 | 90 | 100 |
| | 1.0 | 5 | 100 | 100 | 100 | 100 | 100 | 100 | 92 | 100 |
| | 2.0 | 10 | 100 | — | 100 | 100 | — | 100 | 100 | 100 |
| 12 | 0.5 | 5 | 100 | 100 | 100 | 99 | 100 | 100 | 85 | 100 |
| | 1.0 | 5 | 100 | 100 | 100 | 100 | 100 | 100 | 100 | 100 |
| | 2.0 | — | 100 | — | 100 | 100 | — | 100 | 100 | 100 |
| 53 | 0.5 | 0 | 100 | 98 | — | 100 | — | — | 100 | 100 |
| | 1.0 | 0 | 100 | 100 | — | 100 | — | — | 100 | 100 |
| | 2.0 | — | — | — | — | 100 | — | — | 100 | — |
| 50 | 0.5 | 0 | 100 | 65 | 100 | 99 | 85 | 98 | 92 | 100 |
| | 1.0 | 0 | 100 | 100 | 100 | 100 | 100 | 100 | 100 | 100 |
| | 2.0 | 10 | 100 | — | 100 | 100 | — | 100 | — | 100 |
| 10 | 0.5 | 0 | 100 | 100 | 100 | 100 | 98 | 100 | 100 | 100 |
| | 1.0 | 5 | 100 | 100 | 100 | 100 | 100 | 100 | 100 | 100 |
| | 2.0 | 0 | 100 | — | 100 | 100 | — | 100 | 100 | 100 |
| 63 | 0.5 | 5 | 100 | 100 | 100 | 100 | 100 | 100 | 98 | 100 |
| | 1.0 | 5 | 100 | 100 | 100 | 100 | 100 | 100 | 98 | 100 |
| | 2.0 | 10 | 100 | — | 100 | 100 | — | 100 | 100 | 100 |
| 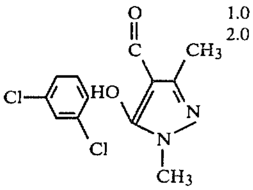 prior art (DE-OS 2,513,750) | 1.0 | 0 | 10 | — | — | 20 | — | 20 | 0 | 0 |
| | 2.0 | 0 | 20 | — | — | — | — | 20 | 0 | 0 |
| 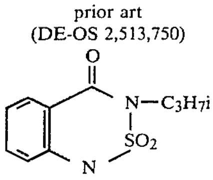 prior art | 1.0 | 0 | 70 | 100 | 100 | 0 | — | 33 | 43 | 80 |
| | 2.0 | 0 | 100 | 100 | 100 | 0 | — | 37 | 55 | 98 |

TABLE 3-continued

| Selective control of unwanted plants in groundnuts; postemergence treatment in the greenhouse | | | | | | | | | | |
|---|---|---|---|---|---|---|---|---|---|---|
| | | Test plants and % damage | | | | | | | | |
| Compound no. | kg/ha | *Arachys hyp.* | *Amar. ret.* | *Abut. theo.* | *Chrys. seg.* | *Echin. c.g.* | *Eleu. ind.* | *Euph. genic.* | Ipomoea spp. | *Sesbania exaltata* |
| (German 1,542,836) | | | | | | | | | | |

0 = no damage, 100 = plants withered

TABLE 4

| Removal of unwanted plants in sorghum and Indian corn; postemergence treatment | | | | | | | |
|---|---|---|---|---|---|---|---|
| | | Test plants and % damage | | | | | |
| Compound no. | kg/ha | *Sorghum bicolor* | *Zea mays* | *Centaurea cyanus* | *Chenopodium album* | *Sesbania exaltata* | *Sinapis alba* |
| 7 | 0.25 | 0 | 12 | 95 | 95 | 97 | — |
| | 0.5 | 10 | 17 | 98 | 100 | 97 | 100 |
| | 1.0 | — | — | 98 | 100 | 100 | 100 |
| 44 | 0.5 | 15 | 15 | 98 | 100 | 100 | 100 |
| | 1.0 | 20 | 18 | 98 | 100 | 100 | 100 |
| 52 | 0.5 | 0 | 10 | 98 | 98 | 80 | 98 |
| | 1.0 | 10 | 10 | 98 | 98 | 100 | 100 |
| 49 | 0.5 | 0 | 20 | 75 | 98 | 90 | 95 |
| | 1.0 | 0 | 20 | 80 | 98 | 100 | 95 |
| 51 | 0.5 | 10 | 15 | 65 | 98 | 80 | 99 |
| | 1.0 | 15 | 20 | 100 | 98 | 100 | 99 |
| 78 | 0.5 | 0 | 20 | 100 | 98 | 100 | 99 |
| | 1.0 | 0 | 20 | 100 | 98 | 100 | 99 |
| 79 | 0.5 | 15 | 25 | 98 | 98 | 100 | 99 |
| | 1.0 | 15 | 25 | 98 | 98 | 100 | 99 |
| 90 | 0.5 | 0 | 10 | 60 | 98 | — | — |
| | 1.0 | 0 | 10 | 75 | 98 | 100 | 80 |

0 = no damage, 100 = plants withered

TABLE 5

| Preemergence use in the greenhouse | | | | |
|---|---|---|---|---|
| | | Test plants and % damage | | |
| Compound no. | kg/ha | *Echin. c.g.* | Lolium *mult.* | Sinapis *alba* |
| 15 | 3.0 | 100 | — | 100 |
| 44 | 3.0 | 70 | 100 | 100 |
| 9 | 3.0 | 70 | 100 | 100 |
| 12 | 3.0 | — | 100 | 100 |
| 48 | 3.0 | — | — | 90 |
| 50 | 3.0 | 70 | 100 | 100 |
| 53 | 3.0 | 100 | 100 | 100 |
| 56 | 3.0 | 70 | — | 100 |
| 52 | 3.0 | 100 | — | 100 |
| 10 | 3.0 | 100 | 100 | 100 |
| 63 | 3.0 | — | 100 | 100 |
| 7 | 3.0 | — | 100 | 100 |
| 47 | 3.0 | — | — | 100 |
| 75 | 3.0 | 100 | 100 | 100 |
| 76 | 3.0 | 100 | — | 100 |
| 78 | 3.0 | 90 | — | 90 |
| 79 | 3.0 | 100 | 80 | 90 |
| 40 | 3.0 | 100 | 100 | 100 |
| 57 | 3.0 | 100 | 100 | 100 |
| 64 | 3.0 | — | 80 | 100 |
| 65 | 3.0 | — | 95 | 100 |
| 49 | 3.0 | 100 | — | 100 |

0 = no effect, 100 = seed not germinated or plants completely withered

TABLE 6

| Control of unwanted plants, postemergence treatment in the greenhouse | | | | | | |
|---|---|---|---|---|---|---|
| | | Test plants and % damage | | | | |
| Compound no. | kg/ha | *Echin c.g.* | *Ipomoea* spp. | *Lamium amplex.* | *Sinapis alba* | Stellaria *media* |
| 66 | 1.0 | 95 | 95 | 95 | 80 | 80 |
| 69 | 1.0 | 95 | 95 | 95 | 80 | 80 |
| 67 | 1.0 | 90 | 95 | 98 | — | 80 |
| 71 | 1.0 | 95 | 95 | 80 | 70 | 70 |
| 70 | 1.0 | 90 | 95 | 95 | 80 | — |
| 124 | 1.0 | 80 | 80 | 95 | 80 | 80 |
| 123 | 1.0 | 80 | 90 | 95 | 70 | 90 |
| 74 | 1.0 | 90 | 95 | 80 | — | 70 |
| 121 | 1.0 | 90 | 90 | 98 | 80 | 70 |
| 87 | 1.0 | 70 | — | 100 | 98 | 90 |
| 83 | 1.0 | 75 | 95 | 100 | 90 | 100 |
| 54 | 1.0 | 100 | 100 | 100 | 70 | 100 |
| 89 | 1.0 | 90 | 98 | 100 | 98 | 100 |

0 = no damage, 100 = plants completely withered

TABLE 7

| Control of wild oats and other unwanted plants in Gramineae crops; postemergence treatment in the greenhouse | | | | | | | | | |
|---|---|---|---|---|---|---|---|---|---|
| | | Test plants and % damage | | | | | | | |
| Compound no. | kg/ha | *Sorgh. bic* | *Tritic. aest.* | *Avena fatua* | *Chenop. album* | *Lamium* spp. | *Sinap. alba* | *Sesb. exal* | *Solan. nig.* |
| 182 | 1.0 | 20 | 15 | 88 | — | 85 | 90 | 100 | 100 |
| 179 | 2.0 | 15 | 10 | 80 | 100 | 100 | 95 | 100 | 100 |
| 196 | 1.0 | — | 0 | 100 | 100 | 100 | 98 | 100 | 100 |
| 55 | 1.0 | — | 10 | 95 | 98 | — | 65 | 70 | — |
| 169 | 1.0 | 10 | — | 90 | — | — | 98 | 100 | 100 |

TABLE 7-continued

| Control of wild oats and other unwanted plants in Gramineae crops; postemergence treatment in the greenhouse | | | | | | | | | | |
|---|---|---|---|---|---|---|---|---|---|---|
| | | Test plants and % damage | | | | | | | | |
| Compound no. | kg/ha | *Sorgh. bic* | *Tritic. aest.* | *Avena fatua* | *Chenop. album* | *Lamium spp.* | *Sinap. alba* | *Sesb. exal* | *Solan. nig.* |
| 23 | 1.0 | 0 | — | 98 | 100 | 100 | 70 | 100 | 95 |
| 42 | 1.0 | 0 | 0 | 90 | 100 | 100 | 65 | 90 | 100 |
| 178 | 1.0 | 10 | — | 90 | 100 | 100 | 99 | 100 | 100 |
| 103 | 1.0 | 0 | 0 | 65 | 98 | 100 | 90 | 100 | 100 |

TABLE 8

| Selective herbicidal action in cotton; postemergence treatment in the greenhouse | | | | | | | |
|---|---|---|---|---|---|---|---|
| | | Test plants and % damage | | | | | |
| Compound no. | kg/ha | *Gossyp. hirs.* | *Amaranth. retrof.* | *Echin. c.g.* | *Ipomoea spp.* | *Sesb. exal.* | *Solan. nig.* |
| 137 | 1.0 | 0 | — | 100 | 92 | 100 | 100 |
| 191 | 1.0 | 0 | 100 | — | — | 100 | 100 |
| 125 | 2.0 | 0 | 100 | 96 | — | 100 | 100 |
| 122 | 2.0 | 0 | 95 | 100 | 95 | 100 | — |
| 190 | 2.0 | 0 | 100 | 95 | 98 | 100 | 100 |
| 197 | 2.0 | 10 | 50 | 99 | 92 | 100 | — |
| 189 | 2.0 | 10 | — | 95 | 98 | 100 | 100 |
| 68 | 2.0 | 0 | — | 95 | 100 | 100 | 100 |

TABLE 9

| Herbicidal action; postemergence treatment in the greenhouse | | | | | |
|---|---|---|---|---|---|
| | | Test plants and % damage | | | |
| Compound no. | kg/ha | *Centaurea cyanus* | *Echin. c.g.* | *Ipomoee spp.* | *Lolium multifl.* |
| 198 | 3.0 | 100 | — | 100 | 100 |
| 216 | 3.0 | 100 | 100 | 100 | 100 |
| 205 | 3.0 | 100 | 95 | 100 | 90 |
| 204 | 3.0 | 100 | 100 | 100 | 90 |
| 203 | 3.0 | 100 | 100 | 100 | 100 |
| 215 | 3.0 | 100 | 80 | 100 | 100 |
| 227 | 3.0 | 100 | 50 | 100 | 50 |
| 222 | 3.0 | 90 | 90 | 100 | 80 |
| 224 | 3.0 | 90 | 80 | 100 | 90 |
| 221 | 3.0 | 100 | 90 | 90 | 100 |
| 223 | 3.0 | 90 | 80 | 80 | — |
| 106 | 3.0 | 100 | 80 | 100 | 80 |
| 84 | 3.0 | 100 | 80 | — | 80 |
| 91 | 3.0 | 100 | 70 | 100 | 100 |
| 128 | 3.0 | 100 | 90 | 100 | 90 |
| 170 | 3.0 | 100 | 90 | 100 | 90 |
| 177 | 3.0 | 100 | — | — | 100 |
| 181 | 3.0 | 100 | 100 | 100 | 90 |
| 201 | 3.0 | 100 | 95 | 100 | 100 |
| 211 | 3.0 | 100 | 95 | 100 | 90 |
| 218 | 3.0 | 100 | 100 | 100 | 90 |
| 217 | 3.0 | 100 | 90 | 100 | — |
| 193 | 3.0 | 100 | 100 | 100 | — |
| 192 | 3.0 | 100 | 80 | 100 | 90 |
| 219 | 3.0 | 100 | 90 | 100 | 90 |
| 61 | 3.0 | 80 | 80 | 40 | 80 |
| 62 | 3.0 | 100 | 90 | 60 | 80 |
| 45 | 3.0 | 100 | 90 | 100 | 100 |
| 195 | 3.0 | 100 | — | 100 | 100 |
| 132 | 3.0 | 100 | 95 | 90 | 60 |
| 212 | 3.0 | 100 | 80 | 95 | 90 |
| 214 | 3.0 | 100 | 95 | 100 | 90 |
| 171 | 3.0 | — | 80 | 60 | 40 |
| 228 | 3.0 | 100 | 100 | 90 | 90 |
| 229 | 3.0 | 100 | 100 | 100 | 100 |
| 230 | 3.0 | 100 | 80 | 100 | 80 |
| 231 | 3.0 | 100 | 100 | 90 | 95 |
| 232 | 3.0 | 100 | 100 | 100 | 100 |
| 233 | 3.0 | 100 | 80 | 90 | 90 |
| 234 | 3.0 | 100 | 20 | 100 | 90 |
| 235 | 3.0 | 100 | 80 | 100 | 90 |
| 236 | 3.0 | 100 | 40 | 100 | 80 |
| 237 | 3.0 | 100 | 40 | 100 | 80 |
| 239 | 3.0 | 100 | 40 | 100 | 100 |

We claim:

1. A pyrazole ether derivative of the formula

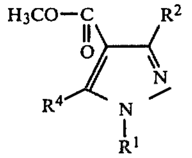

where $R^1$ denotes

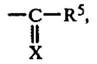

X denoting oxygen and $R^5$ denoting hydrogen, alkyl of 1 to 16 carbon atoms which is unsubstituted or substituted by halogen, or alkoxy of 1 to 4 carbon atoms; alkenyl of 2 to 6 carbon atoms which is unsubstituted or chlorosubstituted; cycloalkyl of 3 to 8 carbon atoms; aralkyl having 1 to 3 carbon atoms in the alkyl and 6 to 10 carbon atoms in the aryl; aryl of 6 to 10 carbon atoms which is unsubstituted or substituted by fluoro, chloro, bromo, alkyl, alkoxy, and haloalkyl all of 1 to 4 carbon atoms, cyano, nitro, alkoxycarbonyl or alkoxycarbonylamino of 1 to 3 alkyl carbon atoms, $R^2$ denotes Y-$R^7$, Y denoting oxygen or sulfur and $R^7$ denoting linear or branched alkyl of 1 to 18 carbon atoms which is unsubstituted or mono- or polysubstituted by fluoro, chloro, bromo, cyano, nitro, cycloalkyl, alkoxy or alkylthio of 1 to 4 carbon atoms; unsubstituted or fluoro-, chloro-, methoxy-, methyl- or trifluoromethyl-substituted aryloxy of 6 to 10 carbon atoms in the aryl; alkoxycarbonyl, alkylaminocarbamoyl or dialkylaminocarbonyl of 1 to 4 carbon atoms in the alkyl; acyloxy of 2 to 4 carbon atoms in the acyl; linear or branched alkenyl of 3 to 18 carbon atoms which is unsubstituted or mono- or polysubstituted by chloro; cycloalkyl of 3 to 8 carbon atoms which is unsubstituted or mono- or polysubstituted by alkyl, alkoxy, haloalkyl of 1 to 4 carbon atoms, fluoro, chloro or bromo; aryl of 6 to 10 carbon atoms which is unsubstituted or mono- or polysubstituted by fluoro, chloro, bromo, cyano, trifluoromethyl, nitro, or by alkyl, alkoxy, alkylthio, alkoxycarbonyl, alkylaminocarbonyl or dialkylaminocarbonyl, each alkyl being of 1 to 4 carbon atoms; aryl of 6 to 10 carbon atoms which is substituted by phenyl or phenoxy which in turn may be substituted by fluoro or chloro; or phenyl substituted by lower ($C_1$ to $C_4$) alkyl esters of (thio)-glycolic acid or (thio)-lactic acid via a (thio)-ether bond, and $R^4$ denotes hydrogen or methyl, and agriculturally acceptable acid addition salts thereof.

2. 1-acetyl-3-cyclopentylmethyloxy-4-methoxycarbonyl-5-methylpyrazole.

* * * * *

UNITED STATES PATENT AND TRADEMARK OFFICE

CERTIFICATE OF CORRECTION

PATENT NO. : 4,298,749

DATED : November 3, 1981

INVENTOR(S) : P. Plath, W. Rohr, B. Wuerzer, and R. Becker

It is certified that error appears in the above—identified patent and that said Letters Patent is hereby corrected as shown below:

IN THE CLAIMS

In claim 1, line 61 of column 44, "alkylaminocarbamoyl" should read --alkylaminocarbonyl--.

Signed and Sealed this

*Thirtieth* Day of *March 1982*

|SEAL|

*Attest:*

GERALD J. MOSSINGHOFF

*Attesting Officer* *Commissioner of Patents and Trademarks*